United States Patent
Frouin et al.

(10) Patent No.: US 11,684,311 B2
(45) Date of Patent: Jun. 27, 2023

(54) DEVICE FOR HUMIDIFYING A TEXTILE ELECTRODE

(71) Applicant: BIOSERENITY, Paris (FR)

(72) Inventors: Marc Frouin, Paris (FR); Marion Gouthez, Paris (FR)

(73) Assignee: BioSerenity, Paris (FR)

( * ) Notice: Subject to any disclaimer, the term of this patent is extended or adjusted under 35 U.S.C. 154(b) by 815 days.

(21) Appl. No.: 16/320,649

(22) PCT Filed: Jul. 27, 2017

(86) PCT No.: PCT/FR2017/052109
§ 371 (c)(1),
(2) Date: Jan. 25, 2019

(87) PCT Pub. No.: WO2018/020169
PCT Pub. Date: Feb. 1, 2018

(65) Prior Publication Data
US 2019/0167192 A1 Jun. 6, 2019

(30) Foreign Application Priority Data

Jul. 27, 2016 (FR) ...................................... 1657238

(51) Int. Cl.
*A61B 5/00* (2006.01)
*A61B 5/24* (2021.01)
(Continued)

(52) U.S. Cl.
CPC .............. *A61B 5/6804* (2013.01); *A61B 5/25* (2021.01); *A61B 5/291* (2021.01); *A61B 5/296* (2021.01);
(Continued)

(58) Field of Classification Search
CPC ....... A61B 5/6804; A61B 5/296; A61B 5/291; A61B 5/25; A61B 5/369; A61B 5/318;
(Continued)

(56) References Cited

U.S. PATENT DOCUMENTS

| 5,645,527 A | 7/1997 | Beck |
| 2013/0172724 A1 | 7/2013 | Ali Mohamed Aziz et al. |

(Continued)

FOREIGN PATENT DOCUMENTS

| CN | 204542120 U | 8/2015 |
| EP | 2407096 A1 | 1/2012 |

(Continued)

OTHER PUBLICATIONS

Translationed Chinese Office Action dated Jun. 1, 2021 in CN Application No. 2021052702083050, a foreign correspondence application of U.S. Appl. No. 16/320,649, 13 pages.

(Continued)

*Primary Examiner* — Adam Z Minchella
(74) *Attorney, Agent, or Firm* — Lee & Hayes, P.C.

(57) ABSTRACT

This invention relates to a device for humidifying a textile electrode (1) comprising a first layer (3); a second layer (5); and a material capable of absorbing and retaining water (4); wherein the material capable of absorbing and retaining water (4) is located between the first layer (3) and the second layer (5); the first layer (3) is impermeable to liquid water and water vapour; and the second layer (5) is permeable to liquid water in a direction extending inwards towards the material capable of absorbing and retaining water, and is impermeable to liquid water and permeable to water vapour in the opposite direction thereto. This invention further relates to a system comprising such a humidification device.

10 Claims, 3 Drawing Sheets

Figure 1:
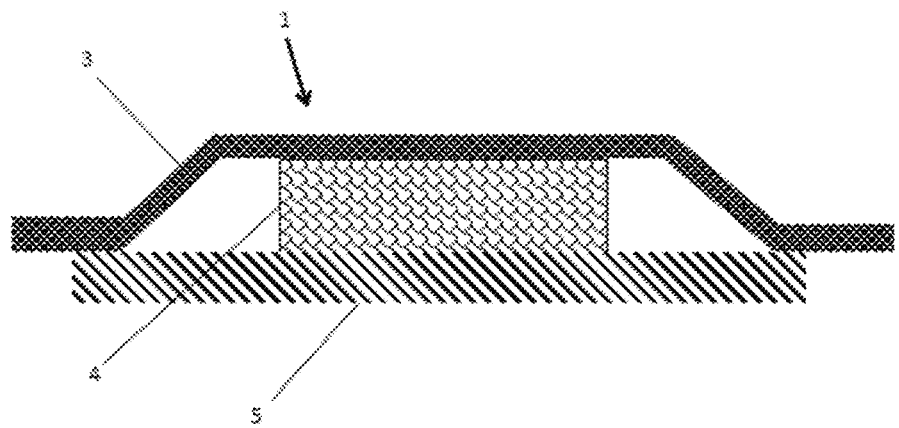

(51) Int. Cl.
*A61B 5/25* (2021.01)
*A61B 5/291* (2021.01)
*A61B 5/296* (2021.01)
*A61N 1/04* (2006.01)
*A61B 5/318* (2021.01)
*A61B 5/369* (2021.01)
*A61B 5/389* (2021.01)

(52) U.S. Cl.
CPC ............... *A61B 5/318* (2021.01); *A61B 5/369* (2021.01); *A61B 5/389* (2021.01); *A61B 2562/0209* (2013.01); *A61B 2562/14* (2013.01); *A61N 1/0472* (2013.01); *A61N 1/0484* (2013.01)

(58) Field of Classification Search
CPC ............ A61B 5/389; A61B 2562/0209; A61B 2562/14; A61N 1/0472; A61N 1/0484; A61F 7/00; A61F 2007/0215; A61F 2007/0214; A61F 2007/0212; A61F 7/02; A61F 2007/0222; A61F 2007/0223
See application file for complete search history.

(56) References Cited

U.S. PATENT DOCUMENTS

| 2014/0005515 | A1* | 1/2014 | Huang | A61B 5/24 600/386 |
| 2014/0039292 | A1* | 2/2014 | Su | A61B 5/276 600/372 |
| 2016/0256676 | A1* | 9/2016 | Freeman | A61N 1/39046 |

FOREIGN PATENT DOCUMENTS

| EP | 2510871 A1 | 10/2012 |
| WO | 2012007384 A1 | 1/2012 |

OTHER PUBLICATIONS

International Search Report dated Nov. 6, 2017 including English-language translation and Written Opinion in corresponding International application No. PCT/FR2017/052109; 8 pages.

* cited by examiner

DEVICE FOR HUMIDIFYING A TEXTILE ELECTRODE

FIELD

This invention relates to a device for automatically humidifying a textile electrode for ExG measurements. In particular, this invention relates to a device for humidifying a textile electrode and the system comprising same.

BACKGROUND

The use of textile electrodes to measure physiological parameters of the human body is known.

However, the use of such textile electrodes is limited as a result of the impedances thereof, which are greater than those obtained via the conventional approach (i.e. when contact is made with the skin via a gel).

To compensate for this, it must be ensured that moisture is present between the electrodes and the skin, to allow ionic conduction to take place between the two interfaces, and thus obtain sufficient conductivity to precisely detect the signal generated by the human body. It is estimated that one gram of water per day on an electrode is typically required for optimal operation.

In many uses, the individual's perspiration is not enough to sufficiently humidify the surface between the conductive layer of the electrode and the skin; the detection of said signals with sufficient quality levels thus becomes difficult.

The conventional approach of using non-textile electrodes consists in placing the metal or conductive electrode in contact with the skin via a gel. The use of such a gel reduces the impedance upon contact of the electrode such that the very low electric signal variations, such as those measured by electroencephalography (EEG), electrocardiography (ECG) or electromyography (EMG), can be easily measured.

In many cases, the use of the gel complicates electrode handling, creating artefacts within the measurement. Moreover, given that the gel dries quickly (in a few hours at best), the use thereof between the electrodes and the skin does not allow measurements to be taken over long periods of time, in particular over more than a few hours, or over periods of time in excess of a day. Therefore, the use of a gel complicates the diagnosis of numerous pathologies, for example cardiac pathologies (atrial fibrillation) or neurological pathologies (epilepsy), for which recordings over longer periods of time are required in order to detect and foresee anomalies.

In order to overcome said difficulties, the prior art proposes the placement of a moisture retainer between the conductive layer and the base (or textile) layer. This moisture retainer can, for example, have a structure similar to that of a sponge. This moisture retainer can absorb and store the liquid in order to increase the moisture level between the conductive layer and the skin and thus improve conductivity. However, this method has several drawbacks. Firstly, the moisture level is not perfectly controlled and the quality of the measurement can vary if the water is released in liquid form and in a heterogeneous manner. Moreover, the presence of too much water will not be sustainable and could deteriorate the link between the moisture retainer and the conductive layer, thus affecting the signal.

The international patent application WO2012/007384 proposes a solution to overcome these drawbacks by adding an impermeable layer onto the side opposite that in contact with the skin, thus reducing the evaporation of the moisture present in the moisture retainer while promoting the direction of transmission. However, this technique only solves part of the problem regarding the transmission of the water that remains in liquid form and does not solve the problems concerning (i) the homogeneity of the transmission of water vapour to the skin, (ii) the liquid surplus between the water retainer and the conductive surface, and (iii) the management of long-duration measurements exceeding 10 to 12 hours.

This invention therefore aims to develop a device for continuously humidifying, by means of water vapour, the transmission of which is controlled, a textile electrode during the use thereof by a human being. The device according to the invention performs this function while controlling the quantities of water vapour transmitted and the transmission areas or surfaces. It prevents the evaporation of moisture when not in use on a person and provides comfort to the user, who does not feel any moisture-related sensations at the start of a cycle.

By controlling the moisture level, the system comprising the humidification device is designed to maintain an optimal electric signal while allowing the wearing thereof over long periods of time, thus providing high-quality measurements. The system according to the invention further allows the person wearing the system to perform activities during the measurements without disruption of the signals as a result of movement artefacts.

Moisture control also ensures operation of the electrode in resistive mode when changing between resistive mode and inductive mode. The effect of the inductive operating mode is particularly sensitive to any minute movements at the level of the contact between the skin and the conductive material. This must therefore be prohibited for outpatient measurements for quality reasons.

The integration of the system is designed to operate within the normal life cycle of a textile: washing, use(s), washing. It provides the advantage of easy self-humidification in a passive manner when being washed, i.e. without any specific action on the device; washing or simply soaking the textile in water allows it to be recharged with water without any further action.

The system is designed such that it is easy to incorporate into an item of clothing and operates within the normal life cycle of a measurement for an individual. During this life cycle, the contact made with the body generates the rise in temperature, which very quickly releases the moisture reserve in the form of a vapour. This provides a known quantity of water that was predetermined during manufacture. Therefore, no specific action need take place on the device. This release can be calibrated in grams of water per day without requiring any further action once the materials and composition have been selected.

Finally, the device according to this invention provides for a sufficient mechanical contact with the skin of the subject, when incorporated into an item of clothing, so as to ensure that an optimal electrical contact is made with the skin with few artefacts.

SUMMARY

The present invention relates to a device for humidifying a textile electrode comprising:
  a first layer;
  a second layer; and
  a material capable of absorbing and retaining water;
  wherein the material capable of absorbing and retaining water is located between the first layer and the second layer;

the first layer is impermeable to liquid water and water vapour; and the second layer is permeable to liquid water in a direction extending inwards towards the material capable of absorbing and retaining water, and is impermeable to liquid water and permeable to water vapour in the opposite direction thereto.

In one embodiment, the first layer is a non-conductive and non-deformable layer.

In one embodiment, the second layer is a deformable layer.

In one embodiment, the second layer is a microporous layer or a hydrophilic layer.

In one embodiment, the device for humidifying a textile electrode further comprises a pocket, the material capable of absorbing and retaining water being contained in said pocket, said pocket being permeable to water in a direction extending inwards towards the material capable of absorbing and retaining water, and permeable to water vapour in the opposite direction thereto.

In one embodiment, the second layer is comprised of at least one first portion and one second portion, the first portion being impermeable to liquid water and permeable to water vapour in a direction extending outwards from the material capable of absorbing and retaining water towards the outside of the device, the second portion being permeable to liquid water in both directions.

In one embodiment, the second portion of the second layer comprises at least one perforation configured such that it is permeable to liquid water at a pressure exceeding atmospheric pressure.

In one embodiment, the device for humidifying a textile electrode further comprises a third layer having a thickness of at least 0.5 mm, said layer being located between the material capable of absorbing and retaining water and the first layer.

The present invention further relates to a system comprising:

a humidification device according to this invention; and a textile support comprising a conductive area forming an electrode;

wherein the textile support is connected to the humidification device such that the conductive area is in contact with the second layer.

In one embodiment, the textile support is connected to the humidification device such that the conductive area is in contact solely with the first portion of the second layer.

DEFINITIONS

In this invention, the terms below shall be understood as follows:

"Textile" is understood as being a material obtained by the assembly of threads, fibres and/or filaments by any method whatsoever, such as by weaving or knitting.

"Deformable" means capable of being deformed, for example under a stress. The deformation is preferably elastic insofar as the deformed body does not break under the effect of the deformation.

"Water" is understood as including any type of liquid allowing for the humidification of the electrodes in order to provide an ionic transfer condition, so as to allow for an optimal electrical and ionic conduction to take place between the electrode and the body of the subject with an acceptable degree of comfort. This can be a pure liquid, a liquid containing impurities or a mixture. Advantageously, this is an aqueous solution.

"Textile electrode" is understood as being a textile support comprising at least one conductive area.

"Impermeable" is understood as not allowing liquids and/or gases to pass.

"Impermeable to liquid" is understood as not allowing liquids to pass, however may allow gases to pass. The material being impermeable to liquids, however permeable to gases, in particular to water vapour.

"ExG" is understood as being electric bio-signals such as, however not limited to those measured by electroencephalography (EEG), electrocardiography (ECG) or electromyography (EMG).

DETAILED DESCRIPTION

The present invention relates to an electrode device comprising a humidification device. Said humidification device comprises a first layer, a second layer and a material capable of absorbing and retaining water. The material capable of absorbing and retaining water is located between the first layer and the second layer. The second layer is that intended to come into contact with the conductive area of a textile support, and the first layer is on the opposite side of the device. The second layer, in contact with the electrode, is impermeable to liquid water and permeable to water vapour from the material capable of absorbing and retaining water as far as the conductive area of the electrode.

The first layer is located, relative to the material capable of absorbing and retaining water, on the side opposite that intended to be connected to the conductive area of the textile support. The first layer is impermeable to liquid water and water vapour. Therefore, the material capable of absorbing and retaining water does not suffer any moisture loss on the side of the first layer, whether in liquid or gaseous form.

In one embodiment, the first layer has a surface area that is greater than or equal to that of the second layer.

In one embodiment, said first layer is made from a non-deformable material. Preferably, the material of the first layer is a poorly deformable material.

In one embodiment, the first layer is made from a non-conductive or electrically insulating material.

In one embodiment, the first layer is made from poly (vinyl chloride) (PVC), polyurethane, silicone film, acrylic polyurethane, or polytetrafluoroethylene (PTFE), etc.

According to the present invention, the second layer is permeable to liquid water in a direction extending inwards towards the material capable of absorbing and retaining water, and is impermeable to liquid water and only permeable to water vapour in the opposite direction thereto.

In one embodiment, said second layer is chemically treated or micro-perforated to make it permeable to water at a pressure and/or vapour pressure exceeding atmospheric pressure.

The permeability of the second layer in the direction extending inwards towards the material capable of absorbing and retaining water allows for the passive recharging of the moisture level of the material capable of absorbing and retaining water. The impermeability to liquid water and the permeability to water vapour of the second layer in the opposite direction thereto allows moisture to pass in the form of water vapour only and therefore allows for the continuous humidification of the electrode by water vapour only.

In one embodiment, the second layer is configured so as to allow about 1 gram of water to pass per day in the form of water vapour outwards from the material capable of absorbing and retaining water when the device is worn by a user and is at a temperature close to body temperature.

In one embodiment, the second layer is configured so as not to allow water to pass in the form of water vapour outwards from the material capable of absorbing and retaining water when the device is at room temperature, preferably when the device is at a temperature close to 20° C.

In one embodiment, the second layer is a deformable layer. This deformability feature of the second layer allows the volume of the humidification device to be adjusted by selecting pressures and vapour pressures imposed by the choice of material. In this manufacturing mode, said layer is designed so as to extend on the side of the second layer and not on the side of the first non-deformable layer. Therefore, the device guarantees, via a volume creating a bulge, an optimal mechanical contact with the skin of the subject in order to provide an optimal electrical contact.

In one embodiment, the second layer comprises microporous membranes and/or hydrophilic membranes. This layer can be a waterproof-breathable membrane. In one alternative embodiment, the waterproof-breathable membrane is a microporous membrane, i.e. water vapour passes through the membrane via micropores. In another embodiment, the waterproof-breathable membrane is a hydrophilic membrane, i.e. water vapour passes through the membrane by capillarity at the chosen pressures. These two types of membranes and combinations thereof can be used to form the second layer.

In one embodiment, the second layer is microporous or mesoporous.

In one embodiment, the second layer is a Goretex®-type membrane or a polyurethane membrane. In one embodiment, the second layer is made from polyester, PU Hydrophile, polyether block amides or polyamide, etc.

According to one embodiment, the second layer comprises or consists of nanoparticles. According to one embodiment, the surface of the second layer comprises or consists of nanoparticles, preferably nanoparticles of inorganic nanoparticles, metal nanoparticles, carbide nanoparticles, oxide nanoparticles, nitride nanoparticles, sulphide nanoparticles, halide nanoparticles, chalcogenide nanoparticles, phosphide nanoparticles, metalloid nanoparticles and/or metal alloy nanoparticles.

According to one embodiment, the inorganic nanoparticles are composed of a material selected in the group of metals, halides, chalcogenides, phosphides, sulfides, metalloids, metallic alloys, ceramics such as for example oxides, carbides, or nitrides. Said inorganic nanoparticles are prepared using protocols known to the person skilled in the art.

According to one embodiment, a chalcogenide is a chemical compound consisting of at least one chalcogen anion selected in the group of O, S, Se, Te, Po, and at least one more electropositive element.

According to one embodiment, the metallic nanoparticles are selected in the group of gold nanoparticles, silver nanoparticles, copper nanoparticles, vanadium nanoparticles, platinum nanoparticles, palladium nanoparticles, ruthenium nanoparticles, rhenium nanoparticles, yttrium nanoparticles, mercury nanoparticles, cadmium nanoparticles, osmium nanoparticles, chromium nanoparticles, tantalum nanoparticles, manganese nanoparticles, zinc nanoparticles, zirconium nanoparticles, niobium nanoparticles, molybdenum nanoparticles, rhodium nanoparticles, tungsten nanoparticles, iridium nanoparticles, nickel nanoparticles, iron nanoparticles, or cobalt nanoparticles.

According to one embodiment, examples of carbide nanoparticles include but are not limited to: SiC, WC, BC, MoC, TiC, $Al_4C_3$, $LaC_2$, FeC, CoC, HfC, or a mixture thereof.

According to one embodiment, examples of oxide nanoparticles include but are not limited to: $SiO_2$, $Al_2O_3$, $TiO_2$, $ZrO_2$, ZnO, MgO, $Sn_{o2}$, $Nb_2O_5$, $CeO_2$, BeO, $IrO_2$, CaO, $Sc_2O_3$, NiO, $Na_2O$, BaO, $K_2O$, PbO, $Ag_2O$, $V_2O_5$, $TeO_2$, MnO, $B_2O_3$, $P_2O_5$, $P_2O_3$, $P_4O_7$, $P_4O_8$, $P_4O_9$, $P_2O_6$, PO, $GeO_2$, $As_2O_3$, $Fe_2O_3$, $Fe_3O_4$, $Ta_2O_5$, $Li_2O$, SrO, $Y_2O_3$, $HfO_2$, $WO_2$, $MoO_2$, $Cr_2O_3$, $Tc_2O_7$, $ReO_2$, $RuO_2$, $Co_3O_4$, OsO, $RhO_2$, $Rh_2O_3$, PtO, PdO, CuO, $Cu_2O$, $Au_2O_3$, CdO, HgO, $Tl_2O$, $Ga_2O_3$, $In_2O_3$, $Bi_2O_3$, $Sb_2O_3$, $PoO_2$, $SeO_2$, $Cs_2O$, $La_2O_3$, $Pr_6O_{11}$, $Nd_2O_3$, $La_2O_3$, $Sm_2O_3$, $Eu_2O_3$, $Tb_4O_7$, $Dy_2O_3$, $Ho_2O_3$, $Er_2O_3$, $Tm_2O_3$, $Yb_2O_3$, $Lu_2O_3$, $Gd_2O_3$, or a mixture thereof.

According to one embodiment, examples of oxide nanoparticles include but are not limited to: silicon oxide, aluminium oxide, titanium oxide, copper oxide, iron oxide, silver oxide, lead oxide, calcium oxide, magnesium oxide, zinc oxide, tin oxide, beryllium oxide, zirconium oxide, niobium oxide, cerium oxide, iridium oxide, scandium oxide, nickel oxide, sodium oxide, barium oxide, potassium oxide, vanadium oxide, tellurium oxide, manganese oxide, boron oxide, phosphorus oxide, germanium oxide, osmium oxide, rhenium oxide, platinum oxide, arsenic oxide, tantalum oxide, lithium oxide, strontium oxide, yttrium oxide, hafnium oxide, tungsten oxide, molybdenum oxide, chromium oxide, technetium oxide, rhodium oxide, ruthenium oxide, cobalt oxide, palladium oxide, gold oxide, cadmium oxide, mercury oxide, thallium oxide, gallium oxide, indium oxide, bismuth oxide, antimony oxide, polonium oxide, selenium oxide, cesium oxide, lanthanum oxide, praseodymium oxide, neodymium oxide, samarium oxide, europium oxide, terbium oxide, dysprosium oxide, erbium oxide, holmium oxide, thulium oxide, ytterbium oxide, lutetium oxide, gadolinium oxide, mixed oxides, mixed oxides thereof or a mixture thereof.

According to one embodiment, examples of nitride nanoparticles include but are not limited to: TiN, $Si_3N_4$, MoN, VN, TaN, $Zr_3N_4$, HfN, FeN, NbN, GaN, CrN, AlN, InN, or a mixture thereof.

According to one embodiment, examples of sulfide nanoparticles include but are not limited to: $Si_yS_x$, $Al_yS_x$, $Ti_yS_x$, $Zr_yS_x$, $Zn_yS_x$, $Mg_yS_x$, $Sn_yS_x$, $Nb_yS_x$, $Ce_yS_x$, $Be_yS_x$, $P_yS_x$, $Ca_yS_x$, $SC_yS_x$, $Ni_yS_x$, $Na_yS_x$, $Ba_yS_x$, $K_yS_x$, $Pb_yS_x$, $Ag_yS_x$, $V_yS_x$, $Te_yS_x$, $Mn_yS_x$, $B_yS_x$, $P_yS_x$, $Ge_yS_x$, $AS_yS_x$, $Fe_yS_x$, $Ta_yS_x$, $Li_yS_x$, $Sr_yS_x$, $Y_yS_x$, $Hf_yS_x$, $W_yS_x$, $Mo_yS_x$, $Cr_yS_x$, $Tc_yS_x$, $Re_yS_x$, $Ru_yS_x$, $Co_yS_x$, $Os_yS_x$, $Rh_yS_x$, $Pt_yS_x$, $Pd_yS_x$, $Cu_yS_x$, $Au_yS_x$, $Cd_yS_x$, $Hg_yS_x$, $Tl_yS_x$, $Ga_yS_x$, $In_yS_x$, $Bi_yS_x$, $Sb_yS_x$, $Po_yS_x$, $Se_yS_x$, $Cs_yS_x$, mixed sulfides, mixed sulfides thereof or a mixture thereof; x and y are independently a decimal number from 0 to 10, at the condition that when x is 0, y is not 0, when y is 0, x is not 0.

According to one embodiment, examples of halide nanoparticles include but are not limited to: $BaF_2$, $LaF_3$, $CeF_3$, $YF_3$, $CaF_2$, $MgF_2$, $PrF_3$, AgCl, $MnCl_2$, $NiCl_2$, $Hg_2Cl_2$, $CaCl_2$, $CsPbCl_3$, AgBr, $PbBr_3$, $CsPbBr_3$, AgI, CuI, PbI, $HgI_2$, $BiI_3$, $CH_3NH_3PbI_3$, $CsPbI_3$, $FAPbBr_3$ (with FA for-mamidinium), or a mixture thereof.

According to one embodiment, examples of chalcogenide nanoparticles include but are not limited to: CdO, CdS, CdSe, CdTe, ZnO, ZnS, ZnSe, ZnTe, HgO, HgS, HgSe, HgTe, CuO, $Cu_2O$, CuS, $Cu_2S$, CuSe, CuTe, $Ag_2O$, $Ag_2S$, $Ag_2Se$, $Ag_2Te$, $Au_2O_3$, $Au_2S$, $Pd_0$, PdS, $Pd_4S$, PdSe, PdTe, PtO, PtS, $PtS_2$, PtSe, PtTe, $RhO_2$, $Rh_2O_3$, $RhS_2$, $Rh_2S_3$, $RhSe_2$, $Rh_2Se_3$, $RhTe_2$, $IrO_2$, $IrS_2$, $Ir_2S_3$, $IrSe_2$, $IrTe_2$, $RuO_2$, $RuS_2$, OsO, OsS, OsSe, OsTe, MnO, MnS, MnSe, MnTe, $ReO_2$, $ReS_2$, $Cr_2O_3$, $Cr_2S_3$, $MoO_2$, $MoS_2$, $MoSe_2$, $MoTe_2$, $WO_2$, $WS_2$, $WSe_2$, $V_2O_5$, $V_2S_3$, $Nb_2O_5$, $NbS_2$, $NbSe_2$, $HfO_2$, $HfS_2$, $TiO_2$, $ZrO_2$, $ZrS_2$, $ZrSe_2$, $ZrTe_2$, $Sc_2O_3$, $Y_2O_3$, $Y_2S_3$, $SiO_2$, $GeO_2$, $GeS$, $GeS_2$, $GeSe$, $GeSe_2$, $GeTe$, $SnO_2$, $SnS$, $SnS_2$, $SnSe$, $SnSe_2$, $SnTe$, $PbO$, $PbS$, $PbSe$, $PbTe$, $MgO$, $MgS$, $MgSe$, $MgTe$, $CaO$, $CaS$, $SrO$, $Al_2O_3$, $Ga_2O_3$, $Ga_2S_3$, $Ga_2Se_3$, $In_2O_3$, $In_2S_3$, $In_2Se_3$, $In_2Te_3$, $La_2O_3$, $La_2S_3$, $CeO_2$, $CeS_2$, $Pr_6O_{11}$, $Nd_2O_3$, $NdS_2$, $La_2O_3$, $T_{12}O$, $Sm_2O_3$, $SmS_2$, $Eu_2O_3$, $EuS_2$, $Bi_2O_3$, $Sb_2O_3$, $PoO_2$, $SeO_2$, $Cs_2O$, $Tb_4O_7$, $TbS_2$, $Dy_2O_3$, $Ho_2O_3$, $Er_2O_3$, $ErS_2$, $Tm_2O_3$, $Yb_2O_3$, $Lu_2O_3$, $CuInS_2$, $CuInSe_2$, $AgInS_2$, $AgInSe_2$, $Fe_2O_3$, $Fe_3O_4$, $FeS$, $FeS_2$, $Co_3S_4$, $CoSe$, $Co_3O_4$, $NiO$, $NiSe_2$, $NiSe$, $Ni_3Se_4$, $Gd_2O_3$, $BeO$, $TeO_2$, $Na_2O$, $BaO$, $K_2O$, $Ta_2O_5$, $Li_2O$, $Tc_2O_7$, $As_2O_3$, $B_2O_3$, $P_2O_5$, $P_2O_3$, $P_4O_7$, $P_4O_8$, $P_4O_9$, $P_2O_6$, $PO$, or a mixture thereof.

According to one embodiment, examples of phosphide nanoparticles include but are not limited to: $InP$, $Cd_3P_2$, $Zn_3P_2$, $AlP$, $GaP$, $TlP$, or a mixture thereof.

According to one embodiment, examples of metalloid nanoparticles include but are not limited to: Si, B, Ge, As, Sb, Te, or a mixture thereof.

According to one embodiment, examples of metallic alloy nanoparticles include but are not limited to: Au—Pd, Au—Ag, Au—Cu, Pt—Pd, Pt—Ni, Cu—Ag, Cu—Sn, Ru—Pt, Rh—Pt, Cu—Pt, Ni—Au, Pt—Sn, Pd—V, Ir—Pt, Au—Pt, Pd—Ag, Cu—Zn, Cr—Ni, Fe—Co, Co—Ni, Fe—Ni or a mixture thereof.

According to one embodiment, the nanoparticles are hydrophobic. According to one embodiment, the nanoparticles are hydrophilic.

According to one embodiment, the second layer comprises or consists of at least one hydrophilic compound, preferably a hydrophilic compound comprising at least one nanoparticle.

According to one embodiment, the second layer comprises or consists of at least one hydrophobic compound, preferably a hydrophobic compound comprising at least one nanoparticle.

According to one embodiment, the second layer comprises or consists of at least one amphiphilic compound, preferably an amphiphilic compound comprising at least one nanoparticle.

According to one embodiment, the second layer comprises or consists of at least one nanoparticle, preferably a nanoparticle comprising a hydrophilic compound.

According to one embodiment, the second layer comprises or consists of at least one nanoparticle, preferably a nanoparticle comprising a hydrophobic compound.

According to one embodiment, the second layer comprises or consists of at least one nanoparticle, preferably a nanoparticle comprising an amphiphilic compound.

According to one embodiment, the surface of the second layer in contact with the electrode, is covered by a substrate of nanoparticles, said nanoparticles being capable of making the surface of the second layer in contact with the electrode impermeable to liquid water. The nanoparticles substrate may be deposited on the second layer in contact with the electrode by plasma type treatments or by coating.

According to one embodiment, the surface of the second layer facing the material capable of absorbing and retaining water is covered by a substrate of nanoparticles, said nanoparticles being capable of making the surface of the second layer facing the material capable of absorbing and retaining water permeable to liquid water. The nanoparticles substrate may be deposited on the second layer facing the material capable of absorbing and retaining water by plasma type treatments or by coating.

According to one embodiment, the second layer comprises or consists of at least one hydrophilic compound, preferably a hydrophilic compound comprising a halogen, more preferably a hydrophilic compound comprising at least one fluorine atom.

According to one embodiment, the second layer comprises or consists of at least one hydrophobic compound, preferably a hydrophobic compound comprising a halogen, more preferably a hydrophobic compound comprising at least one fluorine atom.

According to one embodiment, the second layer comprises or consists of at least one amphiphilic compound, preferably an amphiphilic compound comprising a halogen, more preferably an amphiphilic compound comprising at least one fluorine atom.

According to one embodiment, the second layer comprises or consists of at least one halogen, preferably fluorine. According to one embodiment, the second layer comprises or consists of at least one atom chosen from fluorine (F), chlorine (Cl), bromine (Br) and/or Iodine (I).

According to one embodiment, the surface of the second layer in contact with the electrode, is covered by a compound comprising halogen, preferably fluorine, said compound being capable of making the surface of the second layer in contact with the electrode impermeable to liquid water. The compound substrate may be deposited on the second layer in contact with the electrode by plasma type treatments or by coating.

According to one embodiment, the surface of the second layer facing the material capable of absorbing and retaining water is covered by a compound comprising halogen, preferably fluorine, said compound being capable of making the surface of the second layer facing the material capable of absorbing and retaining water permeable to liquid water. The compound may be deposited on the second layer toward the material capable of absorbing and retaining water by plasma type treatments or by coating.

In one embodiment, the second layer is comprised of at least one first portion and one second portion. In one embodiment, the second layer is comprised of at least one first portion and one second portion in the form of a sandwich, forming a single layer. In one embodiment, the first portion of the second layer is a membrane or a coating. In one embodiment, the second portion of the second layer is a membrane or a coating.

In one embodiment, the first portion of the second layer is impermeable to liquid water and permeable to water vapour in the direction extending outwards from the material capable of absorbing and retaining water towards the outside of the device. In one embodiment, the first portion of the second layer is impermeable to liquid water and water vapour in the direction extending inwards from the outside of the device towards the material capable of absorbing and retaining water.

In one embodiment, the second portion of the second layer is permeable to liquid water in the direction extending inwards from the outside of the device towards the material capable of absorbing and retaining water. Preferably, the second portion of the second layer is permeable to liquid water in the direction extending inwards from the outside of the device towards the material capable of absorbing and retaining water when the pressure applied is greater than atmospheric pressure. In this embodiment, the first portion of the second layer is intended to be in contact with the conductive part of the textile support in order to supply water vapour thereto, said water vapour originating from the water contained in the material capable of absorbing and retaining water. The second portion of the second layer, thanks to the permeability thereof to liquid in the inwards direction, humidifies the material capable of absorbing and retaining water and thus recharges the device for humidifying the textile electrode. Said second portion recharges the water content, in a passive manner, of the material capable of absorbing and retaining water when the device is soaked, for example during washing.

In one embodiment, the second portion of the second layer is not in contact with the material capable of absorbing and retaining water. In one embodiment, the second portion of the second layer is not intended to be in contact with the conductive area of the textile support.

In one embodiment, this permeability to water of the second portion of the second layer is obtained by means of one or more perforations. In one embodiment, the diameter of the perforations lies in the range 0.01 mm to 10 mm Preferably, in order for the material capable of absorbing and retaining water to play its role of retaining water, the one or more perforations must not be in contact with the material capable of absorbing and retaining water so as not to create liquid pressure and so that the latter does not drain via said perforations by capillarity. In this embodiment, the one or more perforations must not be in contact with the conductive area of the electrode so as not to transmit liquid water onto the electrode. In this embodiment, the second portion of the second layer is permeable to liquid water in the direction extending inwards from the outside of the device towards the material capable of absorbing and retaining water as well as in the opposite direction thereto.

In one embodiment, the first and second portion of the second layer are comprised of different materials. In one embodiment, the first and second portion of the second layer are comprised of the same material having undergone different treatments.

The material capable of absorbing and retaining water is located between the first and the second layer. This material ensures the capture then retention of the water in a passive manner, said water being intended to evaporate into vapour form and thus pass through the second layer to humidify the conductive area of the textile support. The material capable of absorbing and retaining water acts as a pump and moisture reservoir between the first layer and the second layer permeable to water vapour.

In one embodiment, the material capable of absorbing and retaining water and selected to perform the expected pump and reservoir functions can be a sponge, superabsorbent polymers (SAPs), hydrogels, alginates, or sugars, etc.

In one embodiment, the material capable of absorbing and retaining water comprises a strong hydrophilic component.

In one embodiment, the material capable of absorbing and retaining water is connected to the second layer. In one embodiment, the material capable of absorbing and retaining water is connected to the second layer over the first portion thereof, but not to the second portion thereof.

In one embodiment, the material capable of absorbing and retaining water is comprised of a single element. In one alternative embodiment, the material capable of absorbing and retaining water is comprised of a plurality of elements, each of which is capable of retaining water. The nature of these different elements can be the same or different.

In one embodiment, the device for humidifying a textile electrode comprises a third layer having a thickness that lies in the range 0.5 mm to 50 mm to meet the mechanical need of bringing the skin and the textile into contact with each other in the position of use of the electrode. In one embodiment, the device for humidifying a textile electrode comprises a third layer having a thickness that is at least equal to 0.5 mm, 1 mm, 2 mm, 3 mm, 4 mm, 5 mm, 10 mm, 15 mm, 20 mm, 25 mm, 30 mm, 35 mm, 40 mm, 45 mm or at least equal to 50 mm Said third layer is located between the material capable of absorbing and retaining water and the first layer. The third layer can be comprised of a plurality of sub-layers that can be stacked on top of each other. The volume and the structure thereof provide a certain volume to the device and thus guarantee an optimised mechanical contact between the electrode and the skin of the subject, thus ensuring that an optimised electrical contact is made with the skin.

The third layer can be made from polyethylene or polyurethane foam for example.

In one embodiment, the third layer is made with sponges, synthetic foams or pads made with bonded fibres (nonwoven materials).

In one embodiment, the device for humidifying a textile electrode comprises a pocket and the material capable of absorbing and retaining water is held in said pocket. In one embodiment, said pocket allows the material capable of absorbing and retaining water to be chosen from a powder or a plurality of elements, in particular a plurality of very small elements. The pocket is located between the first and the second layer. This embodiment is particularly advantageous when the material capable of absorbing and retaining water is comprised of a plurality of elements, in particular very small elements. In one embodiment, said pocket is permeable to water in a direction extending inwards towards the material capable of absorbing and retaining water, and permeable to water vapour in the opposite direction thereto. In one embodiment, said pocket is permeable to water in a direction extending inwards towards the material capable of absorbing and retaining water as well as in the opposite direction thereto. In one embodiment, said pocket is a hydrophilic pocket.

In one embodiment, the pocket is made from polyamide, polyester or cotton fibre.

In one embodiment, in order to guarantee the mechanical strength between the first layer and the second layer, said two layers are connected by any fastening means known to one of ordinary skill in the art. Said fastening means can, for example, be a layer of thermoadhesive polymer, a seam, an ultrasound assembly, rivets, pressures, and spunlacing.

In one embodiment, wherein the material capable of absorbing and retaining water is held inside a pocket, the first layer and the pocket may or may not be connected by any fastening means known to one of ordinary skill in the art. Said fastening means can, for example, be a layer of thermoadhesive polymer, a seam, an ultrasound assembly, rivets, pressures, and spunlacing.

In one embodiment, wherein the device for humidifying an electrode comprises a third layer, the first layer and the third layer are connected by any fastening means known to one of ordinary skill in the art. Said fastening means can, for example, be a layer of thermoadhesive polymer, a seam, an ultrasound assembly, rivets, pressures, and spunlacing.

The invention further relates to a system comprising a humidification device according to this invention, connected to one or more textile electrodes comprised of at least one textile support including a conductive area. The textile support is connected to the humidification device such that the conductive area is in contact with the second layer.

In one embodiment, the conductive area of the textile support is solely connected to the first portion of the second layer.

The textile support is intended to be worn close to the body and provides a good connection of the electrodes to the electronic devices. In one embodiment, the textile support dries faster than the material capable of absorbing and retaining water.

The conductive area of the textile support allows for the detection of the biological signals such as the EEG, ECG or EMG signals. The conductive area of the textile support is in contact with the second layer of the humidification device. The conductive area is intended to be in contact with the skin of the subject and is connected to the humidification device according to this invention, allowing water to pass through in vapour form. As long as the material capable of absorbing and retaining water is damp, the second layer allows the moisture to pass through in the form of water vapour and continuously humidifies the conductive area of the textile support. In one embodiment, the conductive area of the textile support is constituted from a textile coated in silver, or from threads made of stainless steel, carbon, gold, copper, silver, conductive inks (Pedot:Pss, etc.) or any other conductive material (for example carbon filler, silver nanowires, zinc, zinc oxides, silver-plated copper, carbon varnished copper, etc.). In one embodiment, the conductive area of the textile support is porous and coated, impregnated or printed with a conductive material.

In one embodiment, the second layer is connected to the textile support via any fastening means known to one of ordinary skill in the art. Said fastening means can, for example, be a layer of thermoadhesive polymer.

In one embodiment, the first layer has a surface area that is greater than the surface area of the second layer, and is directly connected to the textile support via any fastening means known to one of ordinary skill in the art. Said fastening means can, for example, be a layer of thermoadhesive polymer.

In one embodiment, the first layer and the textile support are connected about the material capable of absorbing and retaining water using a seam.

Preferably, the two latter embodiments aiding the connection between the first layer and the textile support are combined.

The invention further relates to a whole second skin textile comprising at least one humidification device according to this invention or at least one system comprising said device connected to at least one electrode.

When soaking or washing this fabric, the materials capable of retaining water of each system described hereinabove, are charged and allow the textile electrode to be humidified over at least one day, preferably over more than 12 hours.

In one embodiment, the textile comprises a plurality of systems according to this invention.

The invention further relates to an item of clothing intended to be worn by an animal or a human being comprising a textile according to the present invention. This item of clothing can be a T-shirt, an undergarment, an undervest, a pair of trousers, a hat or any other item of clothing that can be worn in contact with the skin. The areas acting as an electrode for each system according to this invention must be in contact with the skin. The subject, when wearing an item of clothing of this type, can undergo regular measurements over a long period of time, over one or more days, without having to humidify the electrodes. When the materials capable of retaining water are dry, the item of clothing can be recharged in a passive manner, i.e. without any specific action on the device by a technician, by the simple soaking thereof in water or the washing thereof by the user. These measurements taken over long periods of time allow, for example, illnesses to be diagnosed such as atrial fibrillation or epilepsy, or allow for monitoring to take place over long periods of time (post-operative monitoring or the monitoring of women experiencing high-risk pregnancies) in a particularly effective manner.

DETAILED DESCRIPTION OF THE FIGURES

FIG. 1 is a cross-sectional view of a humidification device (1) according to one embodiment of the invention. A material capable of absorbing and retaining water (4) is positioned between a first layer (3) and a second layer (5). The first layer (3) is impermeable to liquid water and water vapour, which means that the evaporation of the moisture contained in the material capable of absorbing and retaining water is impossible in this direction. The second layer (5) is impermeable to liquid water but permeable to water vapour in a direction extending outwards from the material capable of absorbing and retaining water (4). Therefore, the electrode located beneath this device, in contact with the second layer (5) will only be humidified by water vapour.

Figure 2:
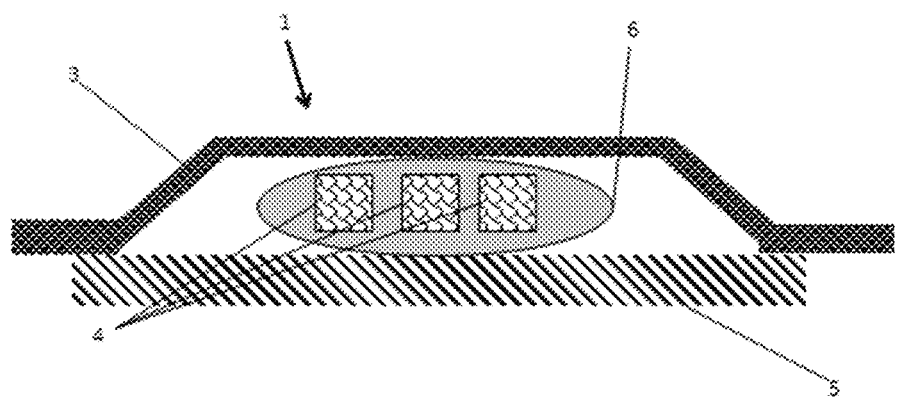

FIG. 2 is a cross-sectional view of a humidification device (1) according to one embodiment of the invention, wherein the material capable of absorbing and retaining water is in three parts (4), and is held in a pocket (6).

Figure 3:
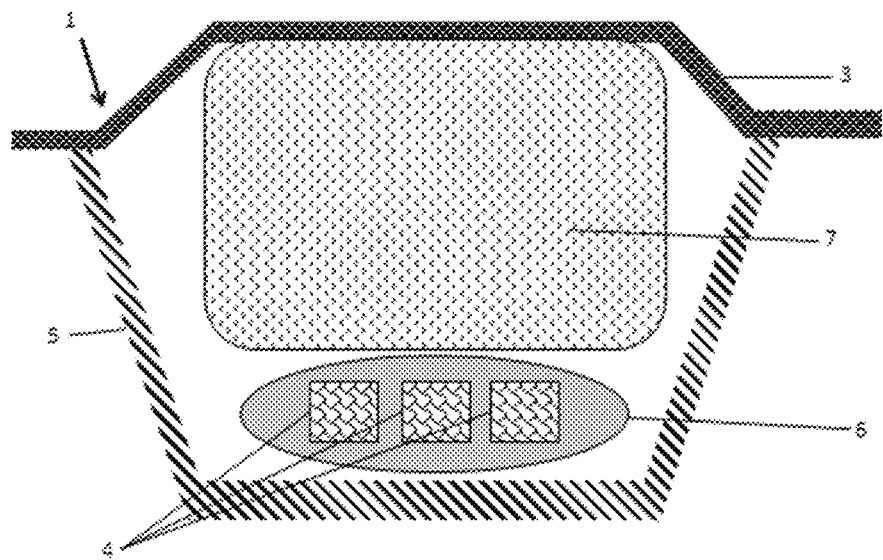

FIG. 3 is a cross-sectional view of a humidification device (1) according to one embodiment of the invention, wherein the material capable of absorbing and retaining water (4) is held in a pocket (6) and wherein a third layer (7) is positioned between the first layer (3) and the pocket (6). Under the pressure of the volume of the third layer, the second deformable layer (5) stretches and the volume therefore extends towards the part intended to be in contact with the skin, aiding the mechanical contact between the electrode and the skin of the subject.

Figure 4:
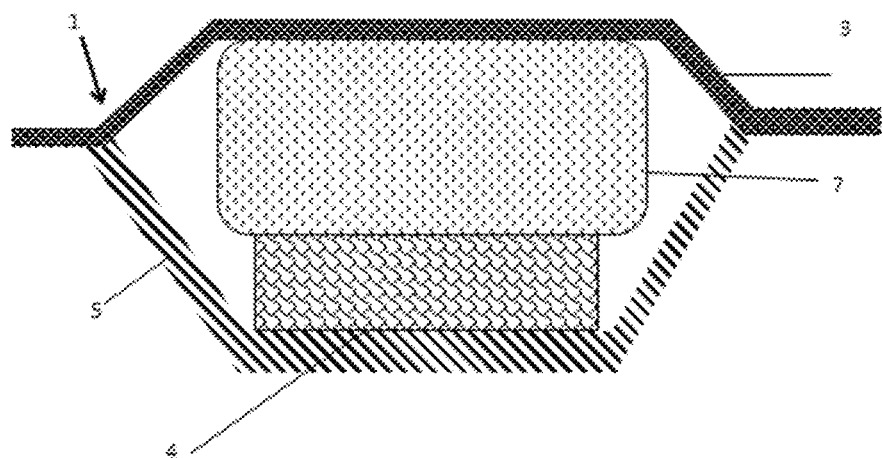

FIG. 4 is a cross-sectional view of a humidification device (1) according to one embodiment of the invention similar to FIG. 3. Unlike in FIG. 3, the material capable of absorbing and retaining water (4) is not located in a pocket, and is comprised of a single element.

Figure 5:
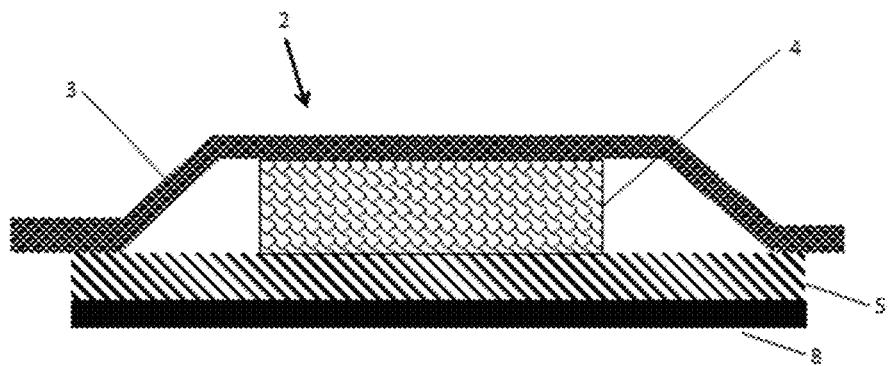

FIG. 5 is a cross-sectional view of a system (2) comprising a humidification device (1) and a textile electrode according to one embodiment of the invention. The conductive area of the textile support (8) is in contact with the second layer (5). When the material capable of absorbing and retaining water (4) is humidified, the conductive area (8) is continuously humidified by water vapour via the second layer (5).

Figure 6:
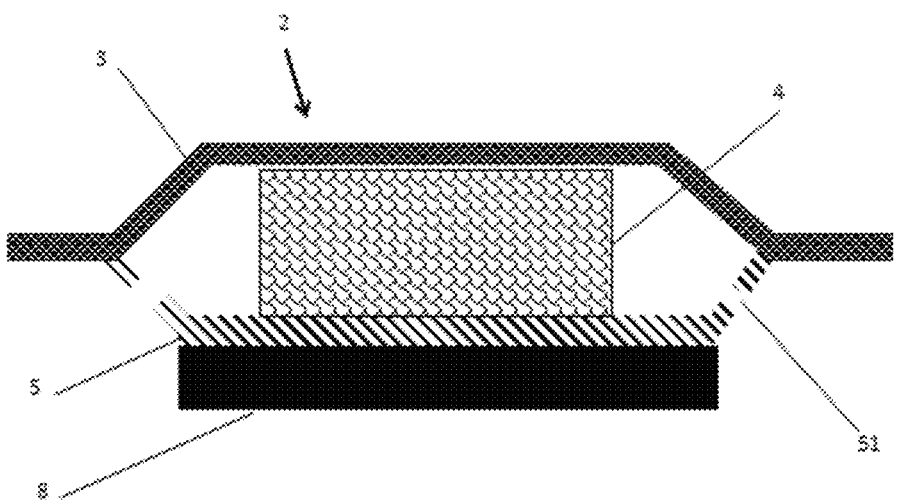

FIG. 6 is a cross-sectional view of a system comprising a humidification device and an electrode according to one embodiment of the invention. In this embodiment, the second layer (5) is comprised of a first portion (connected to the conductive area (8)) and a second portion (that is not connected to the conductive area). Said second portion is permeable to liquid water via perforations (51) that allow the water to enter when passively recharging the electrode (for example during washing). Preferably, the perforations are neither in contact with the material capable of absorbing and retaining water (4), nor in contact with the conductive area (8). In this manner, the material capable of absorbing and retaining water is prevented from being drained of its moisture via said perforations (51).

The invention claimed is:

1. A device for humidifying a textile electrode comprising:
   a first layer;

a second layer; and a material capable of absorbing and retaining water;

wherein the material capable of absorbing and retaining water is located between the first layer and the second layer;

the first layer is impermeable to liquid water and water vapour; and the second layer having a first portion that is arranged to be in contact with a conductive area of a textile support, the first portion being permeable to liquid water in a direction extending inwards towards the material capable of absorbing and retaining water, and is impermeable to liquid water and permeable to water vapour in the opposite direction thereto.

2. The device for humidifying a textile electrode according to claim 1, wherein the first layer is a non-conductive and non-deformable layer.

3. The device for humidifying a textile electrode according to claim 1, wherein the second layer is deformable.

4. The device for humidifying a textile electrode according to claim 1, wherein the second layer is a microporous layer or a hydrophilic layer.

5. The device for humidifying a textile electrode according to claim 1, further comprising a pocket, the material capable of absorbing and retaining water being contained in said pocket, said pocket is permeable to water in a direction extending inwards towards the material capable of absorbing and retaining water, and permeable to water vapour in the opposite direction thereto.

6. The device for humidifying a textile electrode according to claim 1, wherein the second layer further comprises a second portion, the second portion being permeable to liquid water in both directions.

7. The device for humidifying a textile electrode according to claim 6, wherein the second portion of the second layer comprises at least one perforation configured such that it is permeable to liquid water.

8. The device for humidifying a textile electrode according to claim 1, further comprising a third layer having a thickness of at least 0.5 mm, said layer being located between the material capable of absorbing and retaining water and the first layer.

9. A system comprising:
a device comprising:
a first layer;
a second layer; and
a material capable of absorbing and retaining water, wherein the material capable of absorbing and retaining water is located between the first layer and the second layer;
the first layer is impermeable to liquid water and water vapour; and
the second layer having a first portion that is arranged to be in contact with a conductive area of a textile support, the first portion being permeable to liquid water in a direction extending inwards towards the material capable of absorbing and retaining water, and is impermeable to liquid water and permeable to water vapour in the opposite direction thereto; and a textile support comprising a conductive area, wherein the conductive area forms a textile electrode, wherein the textile support is connected to the device such that the conductive area is in contact with the second layer.

10. The system of claim 9,
wherein the second layer further comprises a second portion, the second portion being permeable to liquid water in both directions; and
wherein the textile support is connected to the device such that the conductive area is in contact solely with the first portion of the second layer.

* * * * *